(12) United States Patent
Aminian

(10) Patent No.: US 9,144,440 B2
(45) Date of Patent: Sep. 29, 2015

(54) VERTEBRAL OSTEOSYNTHESIS EQUIPMENT

(71) Applicant: MEDICREA INTERNATIONAL, Neyron (FR)

(72) Inventor: Afshin Aminian, Santa Ana, CA (US)

(73) Assignee: MEDICREA INTERNATIONAL, Neyron (FR)

( * ) Notice: Subject to any disclaimer, the term of this patent is extended or adjusted under 35 U.S.C. 154(b) by 0 days.

(21) Appl. No.: 14/501,956

(22) Filed: Sep. 30, 2014

(65) Prior Publication Data

US 2015/0018885 A1    Jan. 15, 2015

Related U.S. Application Data

(63) Continuation of application No. PCT/IB2013/052625, filed on Apr. 2, 2013.

(60) Provisional application No. 61/620,625, filed on Apr. 5, 2012.

(30) Foreign Application Priority Data

Apr. 4, 2012    (FR) ...................................... 12 53097

(51) Int. Cl.
*A61B 17/70*    (2006.01)

(52) U.S. Cl.
CPC .......... *A61B 17/7053* (2013.01); *A61B 17/7041* (2013.01); *A61B 17/7067* (2013.01); *A61B 17/7071* (2013.01)

(58) Field of Classification Search
CPC ........... A61B 17/7053; A61B 17/7041; A61B 17/7067; A61B 17/7071; A61B 2017/564

USPC .................................................. 606/246-278
See application file for complete search history.

(56) References Cited

U.S. PATENT DOCUMENTS 5,486,174 A * 1/1996 Fournet-Fayard et al. ... 606/261
6,086,590 A * 7/2000 Margulies et al. ............ 606/263
(Continued)

FOREIGN PATENT DOCUMENTS

EP    2279707    2/2011
WO    9855038    12/1998

OTHER PUBLICATIONS

International Search Report issued for corresponding International Patent Application No. PCT/IB2013/052625, mailed Jun. 18, 2013.

*Primary Examiner* — Eduardo C Robert
*Assistant Examiner* — Stuart S Bray
(74) *Attorney, Agent, or Firm* — Myers Wolin, LLC

(57) ABSTRACT

This equipment comprises at least one rigid connecting bar (2), first and second bone anchoring members (3, 4) and first and second connecting parts (5, 6), capable of connecting the connecting bar (2) to said bone anchoring members (3, 4). According to the invention, each second bone anchoring member is in the form of a flexible ligament (4) capable of being engaged around the lamina (101) or an apophysis of a vertebra (100); each second connecting part (6) comprises a conduit (11) receiving said ligament (4) and means (12) for blocking said ligament (4) in the conduit, with tensing of the ligament (4), and each contact member includes at least one rotating part (16; 17) mounted in said second connecting part (6), capable of coming into contact with said connecting bar (2) by a point.

4 Claims, 3 Drawing Sheets

(56) References Cited

U.S. PATENT DOCUMENTS

| | | | |
|---|---|---|---|
| 7,658,739 B2* | 2/2010 | Shluzas | 606/250 |
| 7,914,556 B2* | 3/2011 | Broman et al. | 606/246 |
| 2005/0033295 A1 | 2/2005 | Wisnewski | |
| 2005/0228375 A1* | 10/2005 | Mazda et al. | 606/61 |
| 2007/0088362 A1* | 4/2007 | Bonutti et al. | 606/99 |
| 2008/0262545 A1 | 10/2008 | Simonson | |
| 2009/0105715 A1* | 4/2009 | Belliard et al. | 606/103 |
| 2009/0248077 A1* | 10/2009 | Johns | 606/246 |
| 2009/0259254 A1* | 10/2009 | Pisharodi | 606/246 |
| 2009/0270917 A1* | 10/2009 | Boehm | 606/246 |
| 2009/0326585 A1* | 12/2009 | Baccelli et al. | 606/263 |
| 2010/0023060 A1* | 1/2010 | Bennett et al. | 606/263 |
| 2010/0217323 A1* | 8/2010 | Weirich et al. | 606/256 |
| 2010/0249839 A1* | 9/2010 | Alamin et al. | 606/247 |
| 2010/0249845 A1* | 9/2010 | Meunier et al. | 606/263 |
| 2010/0324600 A1* | 12/2010 | Biyani | 606/264 |
| 2011/0054536 A1* | 3/2011 | Elsebaie et al. | 606/264 |
| 2011/0270314 A1* | 11/2011 | Mueller et al. | 606/264 |
| 2011/0301644 A1* | 12/2011 | Belliard | 606/263 |
| 2012/0022592 A1* | 1/2012 | Belliard | 606/263 |
| 2012/0130373 A1* | 5/2012 | Larroque-Lahitette | 606/74 |
| 2012/0136394 A1* | 5/2012 | Calvosa et al. | 606/254 |
| 2012/0221053 A1* | 8/2012 | Copf | 606/251 |
| 2012/0221057 A1* | 8/2012 | Zhang et al. | 606/264 |
| 2012/0271354 A1* | 10/2012 | Baccelli et al. | 606/263 |
| 2012/0303065 A1* | 11/2012 | Larroque-Lahitette et al. | 606/277 |
| 2013/0012995 A1* | 1/2013 | Butterfield et al. | 606/248 |
| 2013/0023878 A1* | 1/2013 | Belliard et al. | 606/74 |
| 2013/0041410 A1* | 2/2013 | Hestad et al. | 606/263 |
| 2013/0072983 A1* | 3/2013 | Lindquist et al. | 606/278 |
| 2013/0096614 A1* | 4/2013 | Zhang | 606/250 |
| 2013/0268011 A1* | 10/2013 | Rezach et al. | 606/86 A |
| 2014/0094850 A1* | 4/2014 | Clement et al. | 606/263 |
| 2014/0114356 A1* | 4/2014 | Le Couedic et al. | 606/263 |
| 2014/0148854 A1* | 5/2014 | Carlson et al. | 606/254 |
| 2014/0236234 A1* | 8/2014 | Kroll et al. | 606/264 |
| 2014/0257397 A1* | 9/2014 | Akbarnia et al. | 606/263 |
| 2014/0257398 A1* | 9/2014 | Baccelli et al. | 606/263 |
| 2014/0257400 A1* | 9/2014 | George et al. | 606/278 |
| 2014/0257401 A1* | 9/2014 | George et al. | 606/278 |
| 2014/0277207 A1* | 9/2014 | Baccelli et al. | 606/86 A |

* cited by examiner

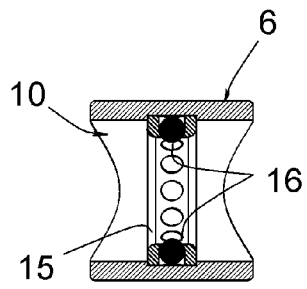
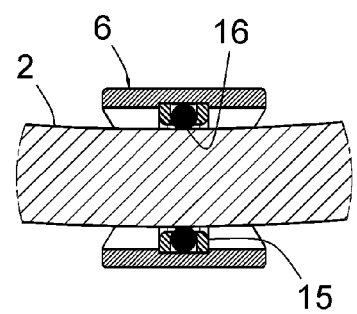
FIG. 5  FIG. 6
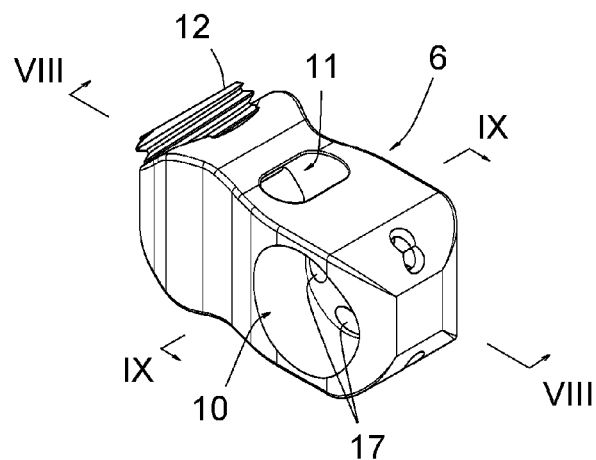
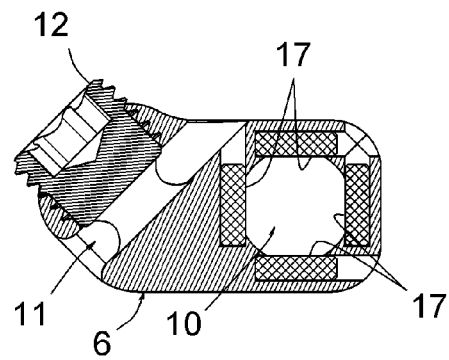
FIG. 7  FIG. 8
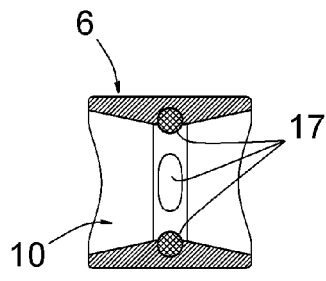
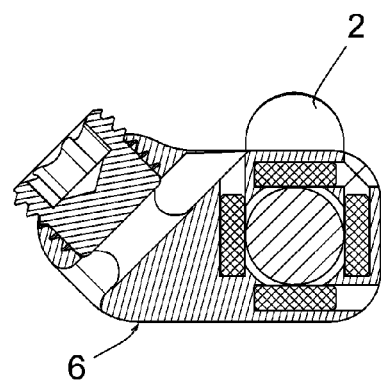
FIG. 9  FIG. 10

VERTEBRAL OSTEOSYNTHESIS EQUIPMENT

CROSS REFERENCE TO RELATED APPLICATIONS

This application is a continuation of International Patent Application No. PCT/IB2013/052625, filed Apr. 2, 2013, now pending, which claims the benefit of U.S. Provisional Application U.S. 61/620,625 filed Apr. 5, 2012, the disclosure of which are herein wholly incorporated by reference. International Patent Application No. PCT/IB2013/052625, filed Apr. 2, 2013 also claims foreign priority to French Patent Application No. FR 12 53097, filed Apr. 4, 2012, now pending, the disclosure of which is herein wholly incorporated by reference.

TECHNICAL FIELD

The present invention relates to vertebral osteosynthesis equipment.

BACKGROUND OF THE INVENTION

It is well known to correct the position of a portion of a vertebral column, or to immobilize such a portion, using vertebral osteosynthesis equipment comprising rigid connecting bars, capable of connecting several vertebrae, bone anchoring members, capable of being anchored in the vertebrae, and connecting parts making it possible to rigidly connect the connecting bars to said bone anchoring members so as to anchor said connecting bars to the vertebrae.

The use of such equipment is, however, problematic when the patient is a child or adolescent, the equipment not being able to adapt itself to the growth of the patient and requiring periodic repeat surgical operations to adapt the position of the connecting parts relative to the connecting bars.

To try to resolve this problem, percutaneously maneuverable systems have been designed. The systems are, however, complex and not fully satisfactory.

Furthermore, the publication of American patent application Nr. US 2011/270314 A1 describes equipment comprising:
- at least one rigid connecting bar, capable of connecting several vertebrae,
- first bone anchoring members and first connecting parts, capable of anchoring the connecting bar to the vertebrae with immobilization of that bar relative to the first connecting parts, and
- second bone anchoring members secured to second connecting parts capable of anchoring the connecting bar to the vertebrae with sliding of the bar relative to the second connecting parts; each of these two bone anchoring members is formed by a screw body and each of these two connecting parts comprises a receiving conduit through which the bar is received slidingly and includes a contact member therein forming a contact interface between said second connecting part and said bar.

In the applicant's opinion, this equipment may be problematic in terms of the complexity of placement and rapid wear of said contact members. Furthermore, a risk of blocking the sliding of the bar relative to said second connecting parts, following the growth of bone cells around said bar and said second connecting parts, cannot be ruled out, thereby making the equipment ineffective.

OBJECT OF THE INVENTION

The present invention aims to resolve these essential problems.

SUMMARY OF THE INVENTION

The equipment according to the invention comprises:
- at least one rigid connecting bar, capable of connecting several vertebrae,
- first bone anchoring members and first connecting parts, capable of anchoring the connecting bar of the vertebrae with immobilization of that bar relative to the first connecting parts, and
- second bone anchoring members and second connecting parts, capable of anchoring the connecting bar to the vertebrae with sliding of the bar relative to the second connecting parts; each second connecting part comprises a receiving conduit through which the bar is received, slidingly, and includes a contact member therein forming a contact interface with said second connecting part and said bar;
- each second bone anchoring member is in the form of a flexible ligament capable of being engaged around the lamina or an apophysis of a vertebra;
- each second connecting part comprises a conduit receiving said ligament and means for blocking said ligament in the conduit, with tensing of the ligament, and
- each contact member includes at least one rotating part mounted in said second connecting part, capable of coming into contact with said connecting bar by a point.

The invention thus provides equipment combining (i) bone anchoring of said second connecting parts using ligaments and (ii) rotating parts forming said contact members, in point contact with the connecting bar.

The applicant was in fact able to determine that the complete resistance of said contact members to wear generated, over a long period of time, by the repeated micro-movements exerted by the vertebrae on that equipment, involved providing said contact members in the form of rotating parts with point contact with the bar. It nevertheless found that the use of such rotating parts involved perfect alignment of the two connecting parts with the connecting bar, which led it to anchor the second connecting parts to the vertebrae using flexible ligaments. In fact, said ligaments, due to their flexibility, make it possible to absorb any alignment flaws of the two connecting parts with the connecting bar, while being able to be fully tensioned between the connecting bar and the vertebrae, using said locking means, so as to enable a correction of the position of said vertebrae.

Furthermore, the applicant was able to determine that the piercing of the vertebrae making it possible, according to the prior art, to screw said second connecting parts in the vertebrae, led to a risk of proliferation of bone cells around said second connecting parts and around the bar, and therefore, over time, to a risk of blocking the sliding made possible by those parts. Using flexible ligaments eliminates any piercing and consequently avoids that risk of proliferation.

A method for implanting the equipment according to the invention comprises the following steps:
- placing said first bone anchoring members and said first connecting parts at a vertebra situated in a central area of the vertebral portion to be straightened or immobilized;
- engaging said flexible ligaments around the laminas or apophyses of one or more vertebrae situated at one end or both ends of the vertebral portion to be straightened or immobilized;

in any order, engaging the ligaments in the receiving conduits comprised by said second connecting parts and engaging said second connecting parts on the connecting bar(s); and tensing the ligaments and tightening said locking means to maintain that tension.

Said at least one contact member can in particular include a series of beads supported by an annular cage placed coaxially to the conduit comprised by said second connecting part for the engagement of the connecting bar.

Said at least one contact member can also include a series of cylinders or rollers mounted freely rotating in cylindrical housings formed in the body of said second connecting part.

BRIEF DESCRIPTION OF THE DRAWINGS

The invention will be understood, and other features and advantages thereof will appear, in reference to the appended diagrammatic drawing, showing, as non-limiting examples, several possible embodiments of the concerned equipment.

FIG. 5 is a cross-sectional view along line V-V of FIG. 3;

FIG. 6 is a view of said connecting part similar to FIG. 5, after the engagement of the connecting bar in the connecting part;

FIG. 7 is a view of the connecting part comprised by said equipment, according to a second embodiment;

FIGS. 8 and 9 are cross-sectional views along lines VIII-VIII and IX-IX, respectively, of FIG. 7;

FIG. 10 is a view of said connecting part similar to FIG. 8, after the engagement of the connecting bar in the connecting part;

DESCRIPTION OF THE PREFERRED EMBODIMENTS

Figure 1:
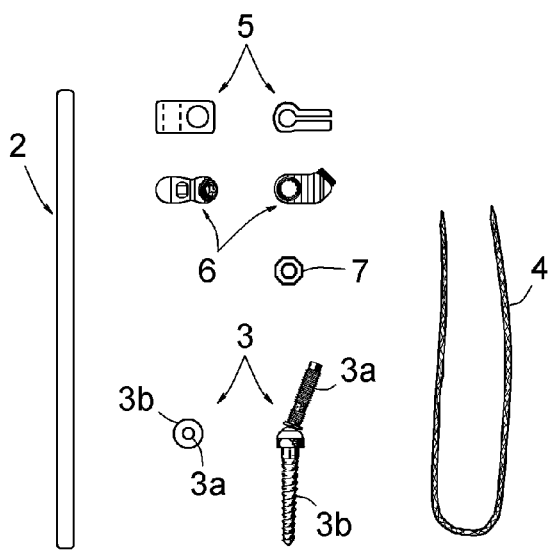
FIG. 1 is a view of the various types of elements comprised by the equipment.

FIG. 1 shows various types of elements comprised by vertebral osteosynthesis equipment, said equipment being particularly designed to treat a growing patient, namely a child or adolescent.

The equipment comprises: two rigid connecting bars 2, capable of connecting several vertebrae, bone anchoring members in the form of polyaxial pedicle screws 3 and ligaments 4, capable of anchoring said connecting bars 2 to the vertebrae, two types of connecting parts 5, 6, making it possible to connect the connecting bars 2 to said bone anchoring members 3, 4, and nuts 7 for tightening the connecting parts 5 on the screws 3. In FIG. 1, only one bar 2 is shown, from the side; two screws 3 are shown, one from the side on the right in FIG. 1, with its articulated proximal slug 3a inclined relative to the base screw body 3b, and the other is shown from the top on the left side of the figure, with said slug 3a in the axis of the body 3b; a single ligament 4 shown in FIG. 1 (the equipment comprises four such ligaments); two connecting parts 5 and two connecting parts 6 are shown, those situated on the right in FIG. 1 being shown from the side and those on the left in said Figure being shown from above.

The connecting bars 2, screws 3, connecting parts 5 and nuts 7 are of a known type, making it possible to anchor the bar 2 so as to be fixed to the vertebrae, i.e., without possibility of the bar 2 moving relative to the vertebrae. In the illustrated example, these elements are as described in document no. WO 98 55038, whereof the applicant is the holder.

Figure 2:
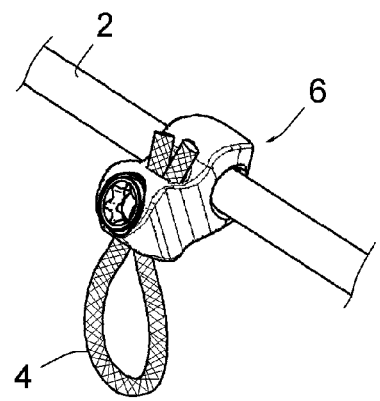
FIG. 2 is a view of some of the elements in the assembled state.
Figure 3:
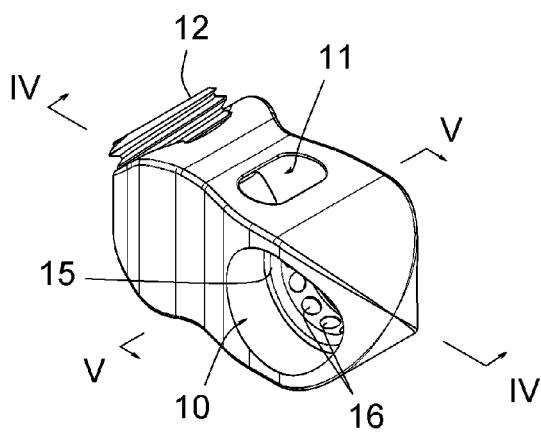
FIG. 3 is a view of a connecting part comprised by said equipment, according to a first embodiment.
Figure 4:
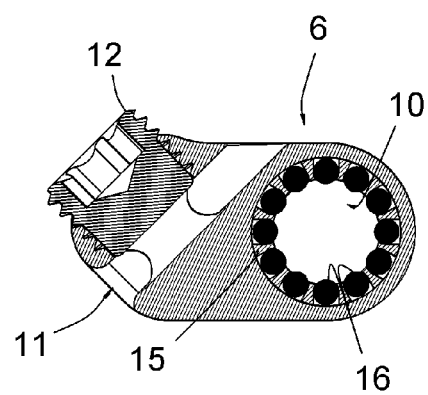
FIG. 4 is a view of said connecting part in cross-section along line IV-IV of FIG. 3.

At least one connecting bar 2 can be rectilinear, as shown in FIG. 1 or 2; it may also be curved, as shown in FIG. 6 or 10, so as to be adapted to the anatomical curvature of the treated vertebral column portion, in particular when it involves the lumbar vertebrae.

It will be understood that the screws 3 and connecting parts 5 maybe of other types; for example, the screws may be of the "tulip" or "top loading" type, in which case the connecting parts are set screws that can be mounted on said screws to immobilize the bars 2 relative to said screws. The screw bodies 3b may be replaced by laminar hooks.

Each ligament 4 is also of a known type, for example made up of a polyester braid, with a circular or flat cross-section.

Figure 12:
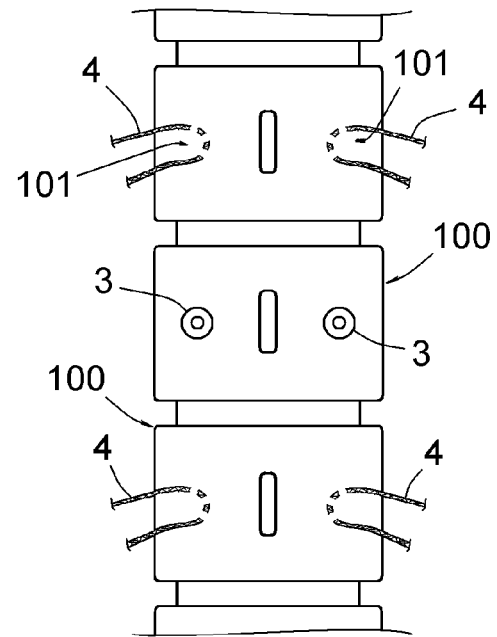
FIG. 12 is a view similar to FIG. 11, after placement of two anchoring pedicle screws in the vertebra situated at the center of said vertebral column portion and the placement of ligaments around the laminas of the superjacent and underlying vertebrae.
Figure 13:
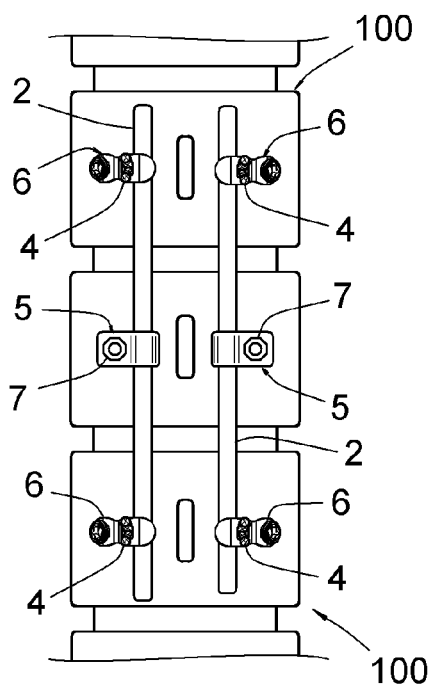
FIG. 13 is a view similar to FIG. 12, after complete placement of the equipment.
Figure 14:
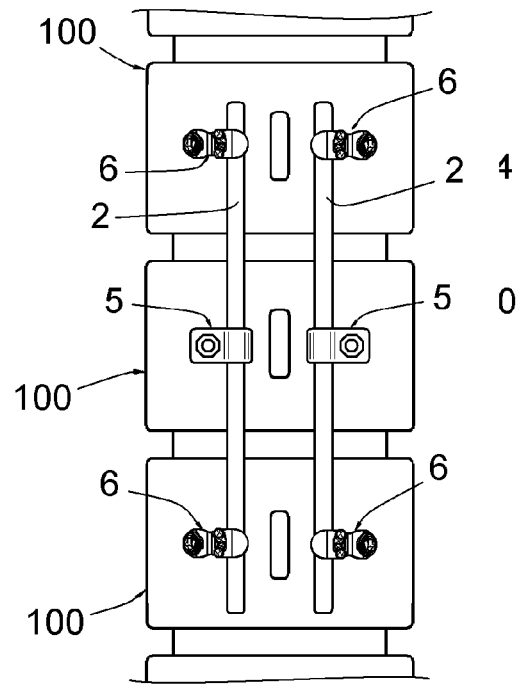
FIG. 14 is a view similar to FIG. 13, following growth of the patient over several months or years.

In reference to FIGS. 3 to 10, it appears that each connecting part 6 comprises a conduit 10 designed to receive the bar 2, as shown in FIGS. 2, 13 and 14, and a conduit 11 designed to receive the two strands of a ligament 4 surrounding the lamina 101 of a vertebra 100 (cf. FIG. 12). The conduit 11 extends in a plane substantially perpendicular to the axis of the conduit 10 and is inclined relative to the conduit 10, with a lower opening of that conduit 11 (i.e., situated for the side of the part 6 designed to be turned toward a vertebra) further from the conduit 10 than the upper opening. A set screw 12 emerges in the conduit 11, making it possible to grip the strands of the ligaments 4 so as to immobilize those strands relative to the part 6.

In the first embodiment shown in FIGS. 3 to 6, the connecting part 6 comprises an annular cage 15 positioned in the conduit 10, coaxial thereto, serving as a seat for a series of beads 16, said beads 16 rolling freely relative to said cage 15. The assembly forms a contact member making up an interface between the second connecting part 6 and the bar 2, such that the bar 2 can easily slide inside the conduit 10.

In the second embodiment of the connecting part 6 shown in FIGS. 3 to 6, this part 6 comprises four cylinders 17 mounted freely rotating in cylindrical housings formed in the body of the part 6.

Figure 11:
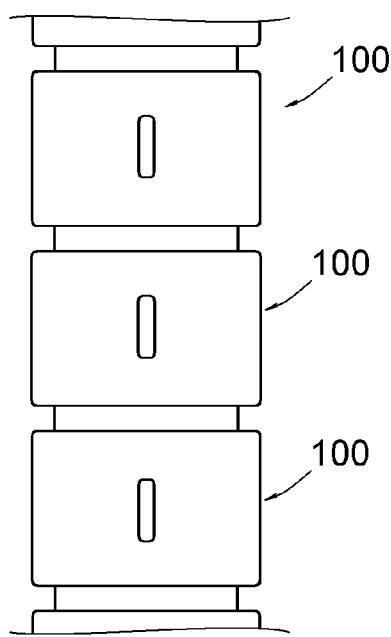
FIG. 11 is a very diagrammatic rear view of a vertebral column portion to be immobilized.

In practice, as shown in FIGS. 11 to 13, the equipment according to the invention is implanted as follows:

implantation of two screws 3 in the pedicles of the vertebra 100 situated at the center of the vertebral column portion to be treated;

engagement of pairs of ligaments 4 around the laminas 101 of the two vertebrae 100 adjacent to the central vertebra (cf. FIG. 12);

rigid connection of the connecting bars 2 to the screws 3 using connecting parts 5;

in any order: sliding engagement of connecting parts 6 on each connecting bar 2, connection of each of the parts 6 to the corresponding ligament 4 by engaging two strands of the ligament 4 in the conduit 11;

tensing the ligament 4 relative to the connecting part 6;

immobilizing said ligament relative to the connecting part 6 by tightening the screw 12 (cf. FIG. 13).

The association of each ligament 4 with the corresponding connecting part 6 makes it possible to obtain anchoring of the connecting bar 2 to said adjacent vertebrae by tensing the ligament 4, then immobilizing the part 6 relative to that ligament; this anchoring does not, however, hinder the possibility of sliding of each connecting part 6 relative to the connecting bar 2.

This possibility of sliding anchoring makes it possible to perform the desired correction or immobilization of a vertebral column segment while enabling the equipment to adapt itself to growth of the patient, as shown by comparing FIGS. 13 and 14.

The invention was described above in reference to the embodiments provided as examples. It is of course not limited to these embodiments, but on the contrary encompasses all other embodiments covered by the appended claims.

What is claimed is:

1. A vertebral osteosynthesis equipment comprising:
at least one rigid connecting bar configured to connect several vertebrae;
first bone anchoring members and first connecting parts wherein the first bone anchoring members anchor the connecting bar to the vertebrae and the first connecting parts connect the connecting bar to the bone anchoring members, such that the connecting bar is immobilized;
second bone anchoring members and second connecting parts wherein the second bone anchoring members anchor the connecting bar to the vertebrae and the second connecting parts connect the connecting bar to the bone anchoring members, such that the connecting bar is configured to slide;
each second connecting part comprises a receiving conduit through which the connecting bar is received, slidingly, and comprises at least one contact member therein forming a contact interface between said each second connecting part and said connecting bar;
each second bone anchoring member is in the form of a flexible ligament configured to engage around a lamina or an apophysis of a vertebra of the several vertebrae;
said each second connecting part comprises a conduit receiving said ligament and at least one screw configured to lock said ligament in the conduit, such that the ligament is maintained under tension;
each at least one contact member comprising at least one rotating part mounted in said each second connecting part, said each at least one contact member in point contact with said connecting bar; and
said each at least one contact member includes a series of beads supported by an annular cage placed coaxially to the conduit comprised by said each second connecting part for the engagement of the connecting bar.

2. A method for implanting vertebral osteosynthesis equipment including at least one connecting bar configured to connect several vertebrae, the method comprising:
placing first bone anchoring members and first connecting parts at at least one vertebra situated in a central area of a vertebral portion to be straightened or immobilized;
engaging flexible ligaments around a laminae or an apophysis of the at least one vertebra situated at one end or both ends of the vertebral portion to be straightened or immobilized, wherein the first bone anchoring members anchor the connecting bar to the least one vertebrae and the first connecting parts connect the connecting bar to the bone anchoring members, such that the connecting bar is immobilized;
in any order, engaging the flexible ligaments in receiving conduits comprised by second connecting parts and engaging said second connecting parts on the connecting bar, wherein the second connecting parts connect the connecting bar to the bone anchoring members, such that the connecting bar is configured to slide;
tensing the flexible ligaments and tightening a lock to maintain the tension,
wherein at least one contact member comprises a series of beads supported by an annular cage placed coaxially to the receiving conduits comprised by said second connecting parts for the engagement of the connecting bar.

3. A vertebral osteosynthesis equipment comprising:
at least one rigid connecting bar configured to connect several vertebrae;
first bone anchoring members and first connecting parts wherein the first bone anchoring members anchor the connecting bar to the vertebrae and the first connecting parts connect the connecting bar to the bone anchoring members, such that the connecting bar is immobilized;
second bone anchoring members and second connecting parts wherein the second bone anchoring members anchor the connecting bar to the vertebrae and the second connecting parts connect the connecting bar to the bone anchoring members, such that the connecting bar is configured to slide;
each second connecting part comprises a receiving conduit through which the connecting bar is received, slidingly, and comprises at least one contact member therein forming a contact interface between said each second connecting part and said connecting bar;
each second bone anchoring member is in the form of a flexible ligament configured to engage around a lamina or an apophysis of a vertebra of the several vertebrae;
said each second connecting part comprises a conduit receiving said ligament and at least one screw configured to lock said ligament in the conduit, such that the ligament is maintained under tension;
each at least one contact member comprising at least one rotating part mounted in said each second connecting part, said each at least one contact member in point contact with said connecting bar; and
said each at least one contact member comprises a series of cylinders or rollers mounted freely rotating in cylindrical housings formed in a body of said each second connecting part.

4. A method for implanting vertebral osteosynthesis equipment including at least one connecting bar configured to connect several vertebrae, the method comprising:
placing first bone anchoring members and first connecting parts at at least one vertebra situated in a central area of a vertebral portion to be straightened or immobilized;
engaging flexible ligaments around a laminae or an apophysis of the at least one vertebra situated at one end or both ends of the vertebral portion to be straightened or immobilized, wherein the first bone anchoring members anchor the connecting bar to the least one vertebrae and the first connecting parts connect the connecting bar to the bone anchoring members, such that the connecting bar is immobilized;
in any order, engaging the flexible ligaments in receiving conduits comprised by second connecting parts and engaging said second connecting parts on the connecting bar, wherein the second connecting parts connect the connecting bar to the bone anchoring members, such that the connecting bar is configured to slide; and tensing the flexible ligaments and tightening a lock to maintain the tension, wherein the at least one contact member includes a series of cylinders or rollers mounted freely rotating in cylindrical housings formed in the body of the second connecting part.

* * * * *